(12) United States Patent
Decou et al.

(10) Patent No.: US 7,260,930 B2
(45) Date of Patent: Aug. 28, 2007

(54) RADIO FREQUENCY-BASED PARTICULATE LOADING MONITORING SYSTEM

(75) Inventors: Mark T. Decou, Peoria, IL (US);
Andrew A. Knitt, Deer Creek, IL (US);
Matthew D. Fike, Peoria, IL (US);
Brian D. Huggins, Peoria, IL (US);
Frank B. Walton, Pinawa (CA)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 11/393,681

(22) Filed: Mar. 31, 2006

(65) Prior Publication Data

US 2007/0022746 A1      Feb. 1, 2007

Related U.S. Application Data

(63) Continuation-in-part of application No. 11/189,530, filed on Jul. 26, 2005, now Pat. No. 7,157,919.

(51) Int. Cl.
*F01N 3/00*      (2006.01)
(52) U.S. Cl. .............................. 60/295; 60/274; 60/275; 60/297; 60/311
(58) Field of Classification Search ................. 60/274, 60/275, 276, 277, 286, 295, 297, 300, 303, 60/311, 312
See application file for complete search history.

(56) References Cited

U.S. PATENT DOCUMENTS 4,477,771 A    10/1984   Nagy et al.

(Continued)

FOREIGN PATENT DOCUMENTS

JP          6-201362        7/1994

OTHER PUBLICATIONS

U.S. Appl. No. 11/189,530, filed Jul. 26, 2005.

*Primary Examiner*—Binh Q. Tran
(74) *Attorney, Agent, or Firm*—Finnegan, Henderson, Farabow, Garrett & Dunner

(57) ABSTRACT

A particulate trap regeneration system is provided, which may include a particulate trap having a filter medium configured to remove one or more types of particulate matter from an exhaust flow of an engine and a regeneration device configured to reduce an amount of particulate matter in the particulate trap, as well as a radio frequency-based particulate loading monitoring system configured to determine an amount of particulate matter trapped by the filter medium. The particulate loading monitoring system may include at least one radio frequency transmitting probe configured to transmit radio frequency signals of predetermined magnitude and predetermined frequency toward the filter medium and at least one radio frequency receiving probe configured to receive and measure the magnitude of received radio frequency signals that pass through the filter medium. Further, the system may include a temperature sensing device configured to take a temperature measurement indicative of a temperature of the particulate trap at the time the radio signals are received by the receiving probe and a controller, which may be configured to determine, based on the measured magnitude of received radio frequency signals, a particulate loading value indicative of the amount of particulate matter trapped in the filter medium. The controller may also be configured to perform a temperature compensation including modifying, based on the temperature measurement, at least one of the following: the measured magnitude of the received radio frequency signals that pass through the filter medium or the particulate loading value.

27 Claims, 4 Drawing Sheets

U.S. PATENT DOCUMENTS

| | | |
|---|---|---|
| 4,580,441 A | 4/1986 | Sakurai et al. |
| 5,157,340 A | 10/1992 | Walton et al. |
| 5,173,662 A | 12/1992 | Trerice et al. |
| 5,177,444 A | 1/1993 | Cutmore |
| 5,195,317 A | 3/1993 | Nobue et al. |
| 5,369,369 A | 11/1994 | Cutmore |
| 5,423,180 A | 6/1995 | Nobue et al. |
| 5,497,099 A | 3/1996 | Walton |
| 6,660,068 B1 * | 12/2003 | Garner et al. ............... 95/283 |
| 6,772,584 B2 * | 8/2004 | Chun et al. .................. 60/275 |
| 6,788,072 B2 | 9/2004 | Nagy et al. |
| 6,938,409 B2 * | 9/2005 | Birckigt et al. ............. 60/275 |
| 6,964,694 B2 | 11/2005 | Rauchfuss et al. |
| 7,157,919 B1 * | 1/2007 | Walton ....................... 324/641 |

* cited by examiner

RADIO FREQUENCY-BASED PARTICULATE LOADING MONITORING SYSTEM

RELATED APPLICATIONS

This application is a continuation-in-part of U.S. patent application Ser. No. 11,189,530, filed Jul. 26, 2005, now U.S. Pat. No. 7,157,919 the entire disclosure of which is incorporated herein by reference.

TECHNICAL FIELD

The present disclosure is directed to a particulate trap regeneration system and, more particularly, to a particulate trap regeneration system having a particulate loading monitoring system.

BACKGROUND

Engines, including diesel engines, gasoline engines, natural gas engines, and other engines known in the art, may exhaust a complex mixture of air pollutants. The air pollutants may be composed of both gaseous and solid material, such as, for example, particulate matter. Particulate matter may include ash and unburned carbon particles and may sometimes be referred to as soot.

Due to increased environmental concerns, exhaust emission standards have become more stringent. The amount of particulate matter and gaseous pollutants emitted from an engine may be regulated depending on the type, size, and/or class of engine. In order to meet these emissions standards, engine manufacturers have pursued improvements in several different engine technologies, such as fuel injection, engine management, and air induction, to name a few. In addition, engine manufacturers have developed devices for treatment of engine exhaust after it leaves the engine.

Engine manufacturers have employed exhaust treatment devices called particulate traps to remove the particulate matter from the exhaust flow of an engine. A particulate trap may include a filter designed to trap particulate matter. The use of the particulate trap for extended periods of time, however, may enable particulate matter to accumulate on the filter, thereby causing damage to the filter and/or a decline in engine performance.

One method of restoring the performance of a particulate trap may include regeneration. Regeneration of a particulate trap filter system may be accomplished by thermal regeneration, which may include increasing the temperature of the filter and the trapped particulate matter above the combustion temperature of the particulate matter, thereby burning away the collected particulate matter and regenerating the filter system. This increase in temperature may be effectuated by various means. For example, some systems employ a heating element (e.g., an electric heating element) to directly heat one or more portions of the particulate trap (e.g., the filter material or the external housing). Other systems have been configured to heat the exhaust gases upstream from the particulate trap, allowing the flow of the heated gases through the particulate trap to transfer heat to the particulate trap. For example, some systems may alter one or more engine operating parameters, such as air/fuel mixture, to produce exhaust gases with an elevated temperature. Running an engine with a "rich" air/fuel mixture can elevate exhaust gas temperature. Other systems heat the exhaust gases upstream from the particulate trap, with the use of a burner that creates a flame within the exhaust conduit leading to the particulate trap.

In some systems, regeneration may be performed continually. In other systems, regeneration may be performed periodically. That is, after a trigger condition occurs, a thermal regeneration system may initiate regeneration in response to the trigger condition. Some systems are configured to initiate regeneration in response to a single type of trigger condition, such as the operation of the engine for a predetermined amount of time or a pressure characteristic of the exhaust system (e.g., backpressure in the exhaust system). Some systems are configured to initiate regeneration in response to measurements of the amount of particulate matter accumulated in the particulate trap. For example, one such regeneration system is disclosed by U.S. Pat. No. 4,477,771 issued to Nagy et al. on Oct. 16, 1984 ("the '771 patent"). The '771 patent discloses a regeneration system configured to initiate regeneration in response to a determination of power loss of microwaves transmitted through the filter medium within a particulate trap.

The system of the '771 patent may be configured to initiate regeneration in response to a determination of power loss of a radio frequency (RF) signal. However, the system of the '771 patent utilizes microwaves rather than low frequency RF signals. For example, the '771 patent discloses use of RF signals having frequencies on the order of 1.85 GHz (1850 MHz). Use of higher frequencies, such as the microwaves used in the '771 patent, requires system components that are more complicated and thus cost more at each stage of development and production. Further, the use of microwaves, as in the '771 patent, often requires a waveguide or resonant chamber. The requirement of such a chamber may limit the design possibilities of a particulate trap housing.

The present disclosure is directed to solving one or more of the problems described above.

SUMMARY OF THE INVENTION

In one aspect, the present disclosure is directed to a particulate trap regeneration system. The system may include a particulate trap having a filter medium configured to remove one or more types of particulate matter from an exhaust flow of an engine and a regeneration device configured to reduce an amount of particulate matter in the particulate trap. The system may also include a radio frequency-based particulate loading monitoring system configured to determine an amount of particulate matter trapped by the filter medium. The particulate loading monitoring system may include at least one radio frequency transmitting probe configured to transmit radio frequency signals of predetermined magnitude and predetermined frequency toward the filter medium. The particulate loading monitoring system may also include at least one radio frequency receiving probe configured to receive and measure the magnitude of received radio frequency signals that pass through the filter medium. Further, the particulate loading monitoring system may include a temperature sensing device configured to take a temperature measurement indicative of a temperature of the particulate trap at the time the radio signals are received by the receiving probe. In addition, the particulate loading monitoring system may include a controller, which may be configured to determine, based on the measured magnitude of received radio frequency signals, a particulate loading value indicative of the amount of particulate matter trapped in the filter medium. The controller may also be configured to perform a temperature compensation including modifying, based on the temperature measurement, at least one of the following: the measured magnitude of the received radio frequency signals that pass through the filter medium or the particulate loading value. The particulate trap regeneration system may also be configured to activate the regeneration device in response to the particulate loading monitoring system detecting more than a predetermined amount of particulate matter trapped in the filter medium.

In another aspect, the present disclosure is directed to a method of regenerating a particulate trap. The method may include determining an amount of particulate matter trapped by a filter medium of a particulate trap configured to remove one or more types of particulate matter from an exhaust flow of an engine. The method may include transmitting radio frequency signals of predetermined magnitude and predetermined frequency toward a filter medium and receiving and measuring the magnitude of received radio frequency signals that pass through the filter medium. The method may also include taking a temperature measurement indicative of a temperature of the particulate trap at the time the radio signals are received. Further, the method may include determining, based on the measured magnitude of received radio frequency signals, a particulate loading value indicative of the amount of particulate matter trapped in the filter medium. In addition, the method may include performing a temperature compensation including modifying, based on the temperature measurement, at least one of the following: the measured magnitude of the received radio frequency signals that pass through the filter medium or the particulate loading value. The method may also include activating a regeneration device, configured to reduce an amount of particulate matter in the particulate trap, in response to the particulate loading monitoring system detecting more than a predetermined amount of particulate matter trapped in the filter medium.

DETAILED DESCRIPTION

Reference will now be made in detail to the drawings. Wherever possible, the same reference numbers will be used throughout the drawings to refer to the same or like parts.

Figure 1:
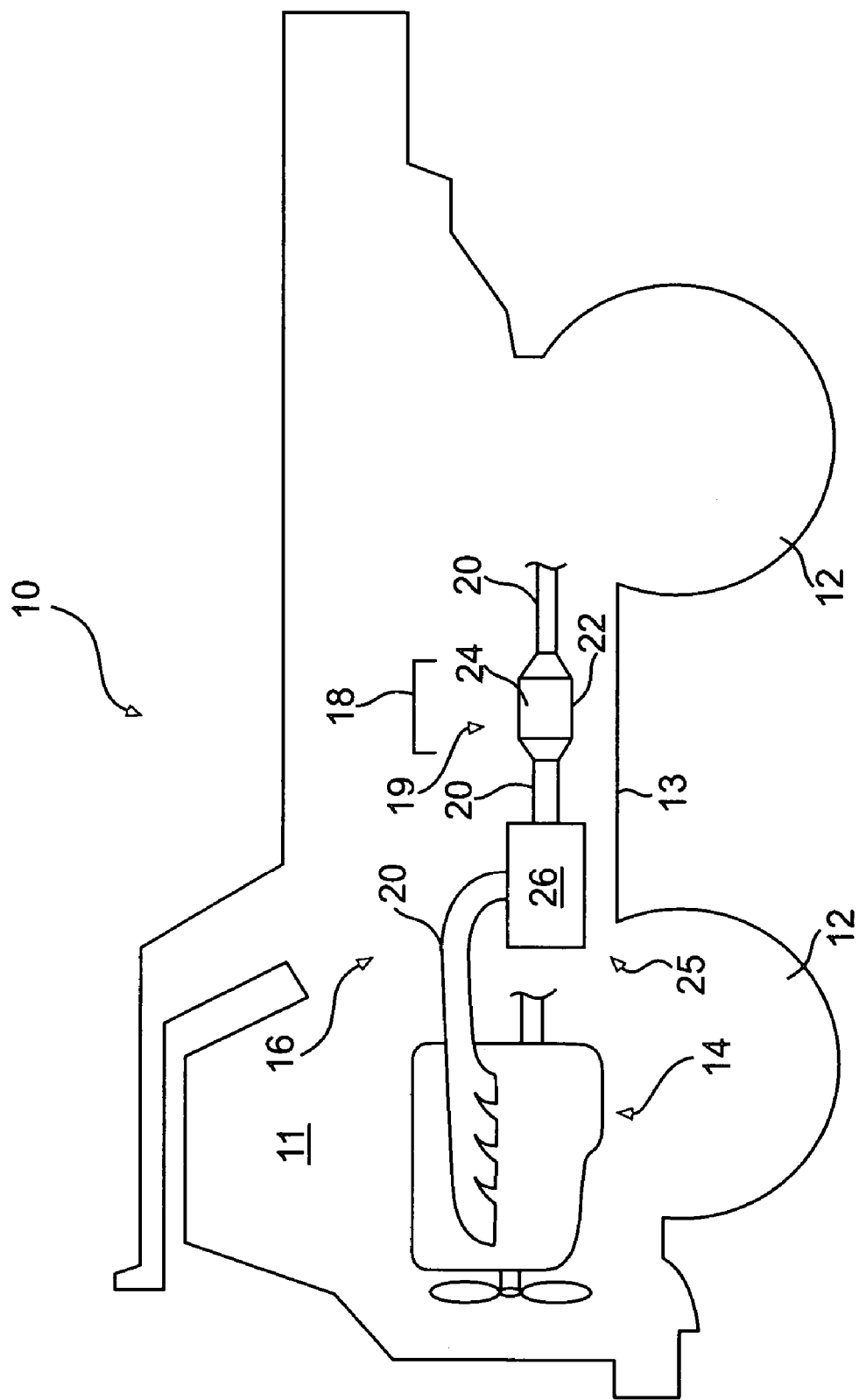
FIG. 1 is a diagrammatic illustration of a machine according to an exemplary disclosed embodiment.

FIG. 1 illustrates a machine 10. Machine 10 may include an operator station 11, one or more traction devices 12, a frame 13, an engine 14, which may be mounted to frame 13, and a particulate trap regeneration system 16.

Although machine 10 is shown as a truck, machine 10 could be any type of machine having an exhaust producing engine. Accordingly, traction devices 12 may be any type of traction devices, such as, for example, wheels, as shown in FIG. 1, tracks, belts, or any combinations thereof.

Engine 14 may be any kind of engine that produces an exhaust flow of exhaust gases. For example, engine 14 may be an internal combustion engine, such as a gasoline engine, a diesel engine, a gaseous fuel burning engine or any other exhaust gas, producing engine.

System 16 may include an after-treatment device 18. After-treatment device 18 may be any type of device configured to remove one or more constituents from the exhaust flow of engine 14. In some embodiments, after-treatment device 18 may be regenerated by heat or some other measure. In one embodiment, after-treatment device 18 may include a particulate trap 19. Particulate trap 19 may be configured to remove one or more types of particulate matter from the exhaust gases produced by engine 14 and flowing through an exhaust conduit 20 configured to direct all or a portion of the exhaust gases produced by engine 14 to after-treatment device 18. Particulate trap 19 may include an outer housing 22, which may encase a filter medium 24 (e.g. a metal mesh or screen, or a porous ceramic material, such as cordierite) configured to remove (i.e., trap) one or more types of particulate matter from the exhaust flow of engine 14.

Although after-treatment device 18 is discussed herein primarily as being a particulate trap, in other embodiments, after-treatment device 18 may include multifunctional devices such as a combination of a catalytic converter and a particulate trap in the same unit or a catalytic particulate trap, wherein filter medium 24 may include a catalytic material and/or a catalytic coating.

After-treatment device 18 may be configured to be thermally regenerated. That is, regeneration of after-treatment device 18 may be accomplished by increasing the temperature of after-treatment device 18. Such increases in temperature of after-treatment device 18 may be generated in a number of different ways. For example, heat may be directly applied to after-treatment device 18 via a heating device integral with or adjacent to after-treatment device 18. An example of such a heating device may include an electric heating element (not shown).

Alternatively or additionally, the temperature of after-treatment device 18 may be increased by heat transferred to it from the exhaust gases flowing through it. In such embodiments, heat may be applied to exhaust gases upstream from after-treatment device 18. The temperature of the exhaust gases may be increased in one or more ways. For example, altering engine parameters may have an effect on exhaust gas temperature. Running engine 14 with a "rich" air/fuel mixture may increase exhaust gas temperature. Increases in engine load may also increase exhaust gas temperature. Exhaust gases may also be heated by post injection, which involves injecting additional fuel into the combustion chambers after the combustion has taken place, which may result in the additional fuel being burned in the exhaust system, thereby elevating the temperature of the exhaust gases in the system.

Exhaust temperature may also be raised by heating the exhaust gases or exhaust conduit 20. For example, an electric heating element and/or flame producing burner may be configured to heat the exhaust gases or exhaust conduit 20. In one embodiment, system 16 may include a regeneration device 25 configured to reduce an amount of particulate matter in after-treatment device 18. For example, regeneration device 25 may include a burner assembly 26 configured to increase the temperature of the exhaust gases flowing through exhaust conduit 20 upstream from after-treatment device 18. Burner assembly 26 may be configured to maintain or restore the performance of after-treatment device 18 through thermal regeneration. Accumulation of exhaust flow constituents in after-treatment device 18 may result in a decline in engine performance and/or possible damage to after-treatment device 18 and/or other components of system 16.

Burner assembly 26 may be configured to prevent or restore any decline in engine performance and avoid possible damage to after-treatment device 18 and/or other components of system 16. For example, burner assembly 26 may be configured to cause at least some of the particulate matter that may have accumulated in after-treatment device 18 to be burned off.

Although system 16 is shown with a single after-treatment device 18 and a single regeneration device 25, system 16 may include more than one after-treatment device 18 and/or more than one regeneration device 25. For example, in one embodiment, system 16 may include a single regeneration device 25 configured to regenerate two after-treatment devices. In another embodiment, system 16 may include two regeneration devices configured to regenerate two after-treatment devices. In such an embodiment, each regeneration device may be configured to regenerate one of the after-treatment devices or contribute to the regeneration of both of the after-treatment devices. System 16 could also include any number of regeneration devices and/or after-treatment devices in any combination suitable for regeneration.

Figure 2:
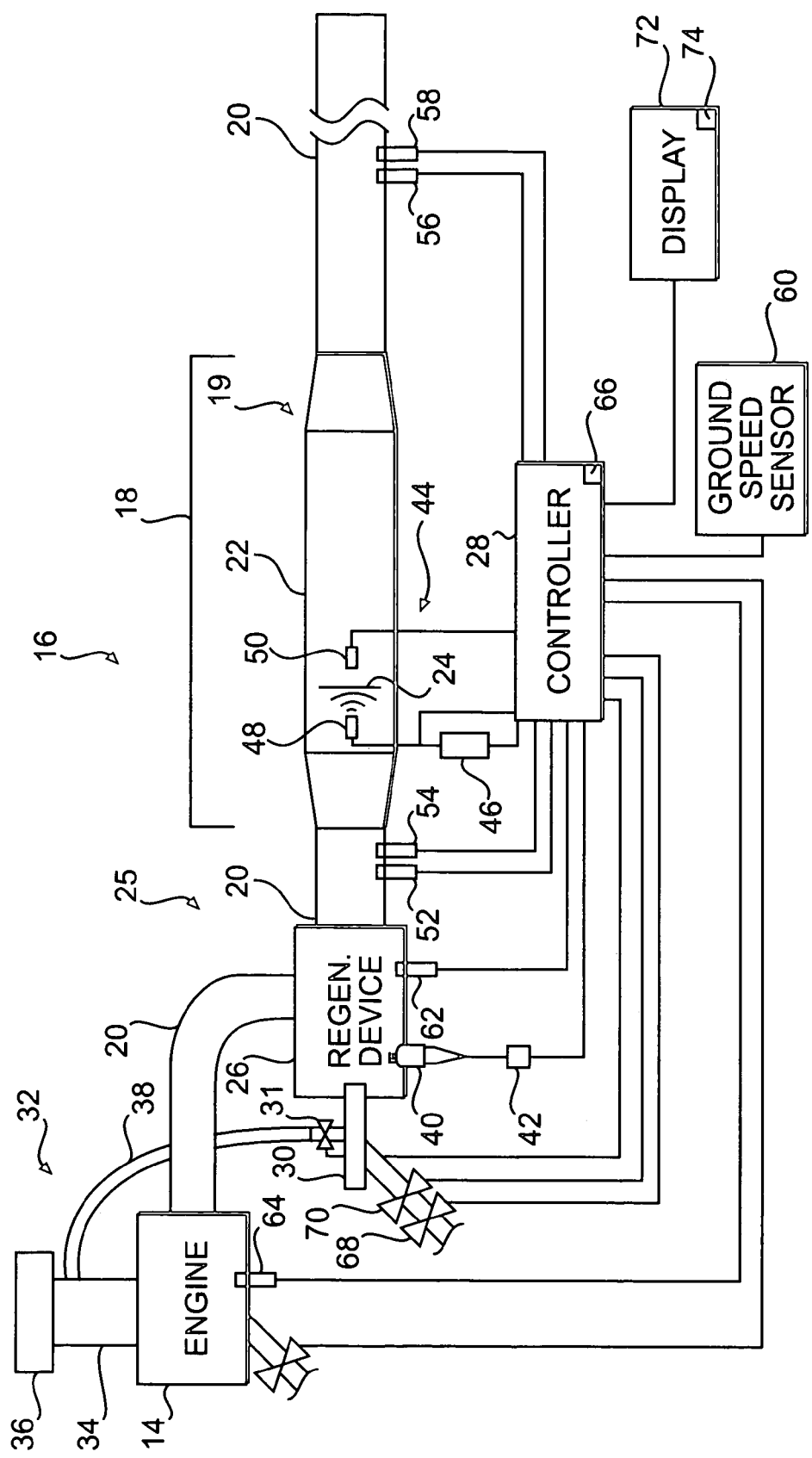
FIG. 2 is a diagrammatic illustration of a particulate trap regeneration system according to an exemplary disclosed embodiment.

FIG. 2 illustrates an exemplary embodiment of particulate trap regeneration system 16. For purposes of the following explanation, after-treatment device 18 will be discussed as being particulate trap 19, while regeneration device 25 will be discussed as being burner assembly 26. However, it should be noted that after-treatment device 18 and regeneration device 25 could be any of the disclosed types of after-treatment and regeneration devices mentioned above. System 16 may also include a controller 28 configured to receive information from various sources and control one or more components of system 16 based on this information.

Burner assembly 26 may be positioned anywhere along exhaust conduit 20 between engine 14 and particulate trap 19. Burner assembly 26 may include a fuel injector 30 configured to supply fuel to burner assembly 26. Burner assembly 26 may be configured to create a flame, which may be in a heat exchange relationship with the exhaust flow. System 16 may be configured to supply fuel injector 30 with fresh air for mixing with the fuel for combustion, as well as for flushing fuel injector 30 of any fuel or debris before and/or after operation of burner assembly 26. The supply of air to fuel injector 30 may be regulated by an air valve 31, controllable by controller 28.

In some embodiments, the source of the fresh air may be an air intake system 32 of engine 14. That is, air may be routed from a portion of air intake system 32, such as an intake manifold 34, downstream from a compressor 36 configured to create forced induction for engine 14. Compressor 36 may include a turbocharger, supercharger, or any other device configured to compress intake air and thereby produce forced induction for engine 14. Air may be directed from intake manifold 34 to fuel injector 30 via an air conduit 38. The supply of air to fuel injector 30 may be regulated by air valve 31, which may be controllable by controller 28 as discussed above.

Burner assembly 26 may also include a spark plug 40 configured to provide spark to ignite the air/fuel mixture delivered by fuel injector 30. Current may be supplied to spark plug 40 by an ignition coil 42, which may be controllable by controller 28. Although burner assembly 26 has been shown and described as including spark plug 40, alternative ignition sources may be employed, such as, for example, glow plugs or any other means for igniting an air/fuel mixture.

System 16 may also include a radio frequency-based particulate loading monitoring system 44 configured to determine an amount of particulate matter trapped by filter medium 24. Each component of particulate loading monitoring system 44 may be located or configured to be located on board machine 10.

Particulate loading monitoring system 44 may include a radio frequency synthesizer 46 configured to deliver radio frequency signals to a radio frequency transmitting probe 48, which may be configured to transmit the radio frequency signals to thereby introduce them to filter medium 24. Particulate loading monitoring system 44 may also include a radio frequency receiving probe 50 configured to receive radio frequency signals that pass through filter medium 24.

Radio frequency transmitting probe 48 and receiving probe 50 may be any of a number of shapes and sizes and may be situated in and/or around filter medium 24 in various ways. The shape and configuration of transmitting probe 48, receiving probe 50, after-treatment device 18, and filter medium 24 may influence the transmission of radio frequency signals through filter medium 24, as well as detection of such transmission. As such, these components may be designed to optimize transmission and reception of a selected frequency or frequency range within one or more filter system geometries.

In addition, particulate loading monitoring system 44 may be further configured to detect magnitudes of radio frequency signals reflected by radio frequency transmitting probe 48 and determine the amount of particulate matter trapped by the filter medium 24 based on the detected magnitudes of radio frequency signals reflected by transmitting probe 48. As more particulate matter accumulates on filter medium 24, the permittivity of filter medium 24 changes. Due to this change in permittivity, the magnitude of RF signal reflected by transmitting probe 48 changes. Therefore, in a calibrated system, detected, reflected RF signals can be used to determine the amount of particulate matter accumulated on filter medium 24. A measurement of reflected RF signal may be used by itself or in conjunction with a measurement of signal loss across filter medium 24 to determine the amount of particulate matter accumulated in filter medium 24.

In some embodiments, particulate loading monitoring system 44 may be configured to transmit a frequency swept signal, i.e., signals of varying frequency within a predetermined band of frequencies. For example, particulate loading monitoring system 44 may be configured to transmit signals of a predetermined magnitude and having frequencies less than about 500 MHz. In certain embodiments, the frequency swept signal may include a band of frequencies between about 100-400 MHz.

Particulate loading monitoring system 44 may be configured to determine RF signal loss across filter medium 24. That is, particulate loading monitoring system 44 may be configured to measure the magnitude of the received radio frequency signals that pass through filter medium 24 and compare the measured magnitude of the received signals of one or more frequencies to the magnitude of the transmitted signals of the same one or more frequencies.

For example, particulate loading monitoring system 44 may be configured to compare the magnitude of signal of each frequency transmitted to the magnitude of signal of the same frequency that is received. The difference between these two magnitudes is the signal loss at that frequency, the value of which may be measured in dB or dBm. Particulate loading monitoring system 44 may be configured to make this determination for each frequency at which a signal is transmitted by transmitting probe 48.

Controller 28 may be configured to determine the amount of particulate loading in particulate trap 19 based on the signal loss value. Alternatively or additionally, controller 28 may be calibrated to convert the measured magnitude of received and/or reflected radio frequency signals directly to a particulate loading value.

Controller 28 may include any means for receiving machine operating parameter-related information and/or for monitoring, recording, storing, indexing, processing, and/or communicating such information. These means may include components such as, for example, a memory, one or more data storage devices, a central processing unit, or any other components that may be used to run an application.

Although aspects of the present disclosure may be described generally as being stored in memory, one skilled in the art will appreciate that these aspects can be stored on or read from types of computer program products or computer-readable media, such as computer chips and secondary storage devices, including hard disks, floppy disks, optical media, CD-ROM, or other forms of RAM or ROM. Various other known circuits may be associated with controller 28, such as power supply circuitry, signal-conditioning circuitry, solenoid driver circuitry, communication circuitry, and other appropriate circuitry.

Controller 28 may perform multiple processing and controlling functions, such as, for example, engine management (e.g., controller 28 may include an engine control module, a.k.a. an ECM), monitoring of particulate loading, and controlling regeneration of particulate trap 19. Alternatively, machine 10 may include multiple controllers (a configuration shown in FIGS. 3 and 4), each dedicated to perform one or more of these or other functions. Such multiple controllers may be configured to communicate with one another. For example, particulate loading monitoring system 44 may include a first controller/processor, which may be configured to determine the amount of particulate matter accumulated in filter medium 24 based on the signals transmitted by transmitting probe 48 and those detected by receiving probe 50, as well as detected power reflected by transmitting probe 48. Such a dedicated controller may also be configured to forward this determination of particulate accumulation to a second controller/processor, which may be configured to control regeneration in response to such information from the first controller.

Controller 28 may be configured to receive the signals detected by receiving probe 50 or information about such signals. Controller 28 may be further configured to activate regeneration device 25 in response to particulate loading monitoring system 44 detecting more than a predetermined amount of particulate matter trapped in filter medium 24.

Controller 28 may also be configured to activate regeneration device 25 in response to one or more other trigger conditions. These other trigger conditions may include, for example, operation of engine 14 for a predetermined amount of time; consumption of a predetermined amount of fuel by engine 14; detection of an elevated backpressure upstream of particulate trap 19 above a predetermined pressure; detection of a pressure differential across particulate trap 19 of greater than a predetermined amount; and a determination that a calculated amount of particulate matter accumulated in particulate trap 19 is above a predetermined amount.

Regeneration may also be initiated manually by an operator, owner, service technician, etc. of machine 10. Manually triggering regeneration may be accomplished via a switch, button, or the like associated with machine 10 and/or a service tool configured to interface with machine 10.

System 16 may include various sensors configured to generate information about operating parameters of system 16. Such information may be received by controller 28. For example, system 16 may include an upstream temperature sensor 52, an upstream pressure sensor 54, a downstream temperature sensor 56, and a downstream pressure sensor 58. Such sensors may be positioned along exhaust conduit 20 upstream and downstream from particulate trap 19 respectively and configured to take measurements of the temperature and pressure of the exhaust gases within exhaust conduit 20 at their respective locations. Such measurements may be received by controller 28.

Upstream pressure sensor 54 and downstream pressure sensor 58 may constitute a pressure differential measurement system. Such a system may be configured to measure a pressure differential between an upstream pressure of the exhaust flow upstream from particulate trap 19 and a downstream pressure of the exhaust flow downstream from particulate trap 19. Alternatively, in lieu of upstream pressure sensor 54 and downstream pressure sensor 58, the pressure differential measurement system may include a single pressure differential sensor (not shown) configured to measure the difference in pressure between the exhaust flow upstream and downstream of particulate trap 19.

System 16 may also include a ground speed sensor 60 configured to monitor the ground speed of machine 10 (i.e., the speed of machine 10 relative to the surface over which it travels). System 16 may also be provided with a flame sensing system associated with burner assembly 26 and configured to detect whether burner assembly 26 is currently producing a flame. Such a flame sensing system may include, for example, a flame sensor 62. In addition, system 16 may include an engine speed sensor 64 configured to measure the speed at which engine 14 is operating (i.e., rpm).

The aforementioned sensors may include any type of sensing means suitable for monitoring their respective parameters. In particular, flame sensor 62 may include any type of sensor suitable for detecting the presence of a flame, such as temperature sensors (e.g., thermocouples), optical sensors, ultraviolet sensors, and ion sensors. Flame sensor 62 may be configured to detect a condition (e.g., temperature, ultraviolet light, ions, etc.) in proximity to the flame. Such a condition may be monitored at any location within close enough proximity to the flame to enable the presence of the flame to be detected. Additionally or alternatively, the flame sensing system may be configured to detect a rate of change in the condition. For example, a temperature in proximity to the flame location that is increasing at a predetermined rate may indicate that a flame is lit and causing the increase In addition or as an alternative to flame sensor 62, upstream temperature sensor 52 may be located upstream of burner assembly 26. In such an embodiment the flame sensing system may be configured to determine whether the downstream exhaust temperature measured by downstream temperature sensor 56 exceeds the upstream exhaust temperature measured by upstream temperature sensor 52 by a predetermined amount. A significantly higher downstream temperature may indicate that the flame is lit and is thus heating exhaust gases as they flow through burner assembly 26.

In some embodiments, upstream temperature sensor 52 or any other temperature sensing device may be configured to take a temperature measurement indicative of a temperature of particulate trap 19. Such temperature measurements may be taken in a manner suitable for determining the temperature of particulate trap 19 at the time the radio signals are received by receiving probe 50. Controller 28 may be configured to determine, based on the measured magnitude of radio frequency signals received by receiving probe 50, a particulate loading value indicative of the amount of particulate matter trapped in filter medium 24. Controller 28 may also be configured to perform a temperature compensation, which may include modifying, based on the temperature measurement, at least one of the following: the measured magnitude of the received radio frequency signals that pass through the filter medium or the particulate loading value. In embodiments configured to determine a signal loss value, the signal loss value may be modified to facilitate the temperature compensation.

The temperature compensation may involve a function that is based on the temperature measurement and at least one of the following: the measured magnitude of the received radio frequency signals that pass through filter medium 24 or the particulate loading value. In some embodiments the function may be based on a signal loss value. Further, in some embodiments, the function may be a third order polynomial. That is, the determination of actual particulate loading may be a function of the temperature measurement and observed particulate loading, which may be represented by the measured magnitude of the received radio frequency signals that pass through filter medium 24, the signal loss value, and/or the particulate loading value. Alternatively, the temperature compensation may involve a look-up table based on the temperature measurement and observed particulate loading, as represented by the aforementioned values.

Controller 28 may include a timing device 66. Controller 28 may be configured to couple information from timing device 66 with information from other sources. For example, controller 28 may utilize information from timing device 66 in conjunction with information regarding operation of engine 14 (e.g., from engine speed sensor 64 to determine how long engine 14 is operated. Timing device 66 may also be used to monitor and control duration of regeneration events or any other operating parameters of system 16 and/or machine 10.

System 16 may be configured to control one or more additional system functions and/or parameters. Controller 28 may be configured to control the pressure of the fuel delivered to fuel injector 30 (and therefore the rate of fuel injection). A fuel on/off valve 68, which may be controllable by controller 28, may be associated with fuel injector 30 to selectively allow fuel to be delivered to fuel injector 30. In addition to fuel on/off valve 68, system 16 may also include a fuel pressure regulator valve 70 controllable by controller 28 to regulate the pressure of the fuel, and thereby the rate at which fuel is delivered to fuel injector 30. In some embodiments, controller 28 may be configured to control the pressure of fuel delivered to fuel injector 30 in a closed loop fashion, i.e., in response to pressure measurements taken at or near fuel injector 30 (e.g., by a fuel pressure sensor, not shown).

Controller 28 may be further configured to control fuel on/off valve 68 and/or fuel pressure regulator valve 70 (i.e., flow of fuel to fuel injector 30) in response to other parameters of system 16. For example, controller 28 may be configured to control the temperature of exhaust gases entering particulate trap 19 in response to feedback from upstream temperature sensor 52. This upstream exhaust temperature may be controlled by regulating the amount of fuel and/or air supplied to fuel injector 30, which may be accomplished by controlling fuel on/off valve 68 and/or fuel pressure regulator valve 70. Other types of regeneration devices or methods may be controlled in response to measurements taken by upstream temperature sensor 52. For example, the amount of post injection may be varied (e.g., by controller 28) to control the temperature of the exhaust gases entering any kind of after-treatment device 18.

System 16 may include multiple fuel pressure regulator valves, which may be independently controlled. At least one fuel pressure regulator valve 70 may be configured to regulate main fuel pressure, and a second fuel pressure regulator valve (not shown) may be configured to regulate pilot fuel pressure. Pilot fuel pressure may be used during a pilot mode in which system 16 utilizes a predetermined air/fuel mixture to prevent flameouts during various engine operating conditions, e.g., hard accelerations and rapid decelerations.

Other operating parameters of system 16 may be monitored to maintain and/or optimize control of the regeneration process. For example, downstream temperature sensor 56 may detect whether downstream exhaust temperature is above a predetermined temperature. If downstream exhaust temperatures get too high, it could be an indication that temperatures within particulate trap 19 may be at an undesirably high level as well and/or that the regeneration may be somewhat unstable (e.g., incineration of particulate matter and/or a catalyst driven reaction may be intensifying within after-treatment device 18 beyond a level commanded by controller 28).

System 16 may also be configured to monitor the stability of the regeneration process by determining a difference between the upstream exhaust temperature measured by upstream temperature sensor 52 and the downstream exhaust temperature measured by downstream temperature sensor 56. If the temperature measured by downstream temperature sensor 56 exceeds that measured by upstream temperature sensor 52 by more than a predetermined amount for more than a predetermined amount of time, controller 28 may initiate steps to scale back or terminate the regeneration process. For example, in such a case, controller 28 may reduce the intensity of the flame produced by burner assembly 26. In some circumstances, controller 28 may terminate the regeneration process if the regeneration process is significantly unstable. For example, if the downstream exhaust temperature exceeds a predetermined value or it exceeds the upstream exhaust temperature by more than a predetermined amount, then controller 28 may terminate the regeneration process.

Controller 28 may be configured to log faults when the downstream exhaust temperature exceeds a predetermined temperature or when the downstream exhaust temperature exceeds the upstream exhaust temperature by more than a predetermined amount. Controller 28 may also be configured to terminate the regeneration process if the number of faults reaches a predetermined value (e.g., when three faults have occurred).

System 16 may include a display 72. Display 72 may be located at any suitable location on machine 10, such as, for example, in operator station 11. Display 72 may be any kind of display, including screen displays, such as, for example, cathode ray tubes (CRTs), liquid crystal displays (LCDs), plasma screens, and the like. Display 72 may be configured to display information about operating parameters of system 16. In one embodiment, display 72 may include a warning indicator 74 (e.g., a warning lamp, warning message, etc.). Controller 28 may be configured to illuminate warning indicator 74 upon detection of the predetermined amount of faults. As an alternative or in addition to display 72, system 16 may include one or more audible alerts for conveying information about operating parameters of system 16 to an operator. In addition to providing visual feedback regarding operating parameters of system 16, display 72 may also be configured to display other information regarding system 16 or any other device and/or system associated with machine 10. Display 72 may also be configured to indicate when a regeneration event is occurring or about to occur. Alternatively or additionally, display 72 may be configured to display information regarding particulate loading monitoring system 44.

Figure 3:
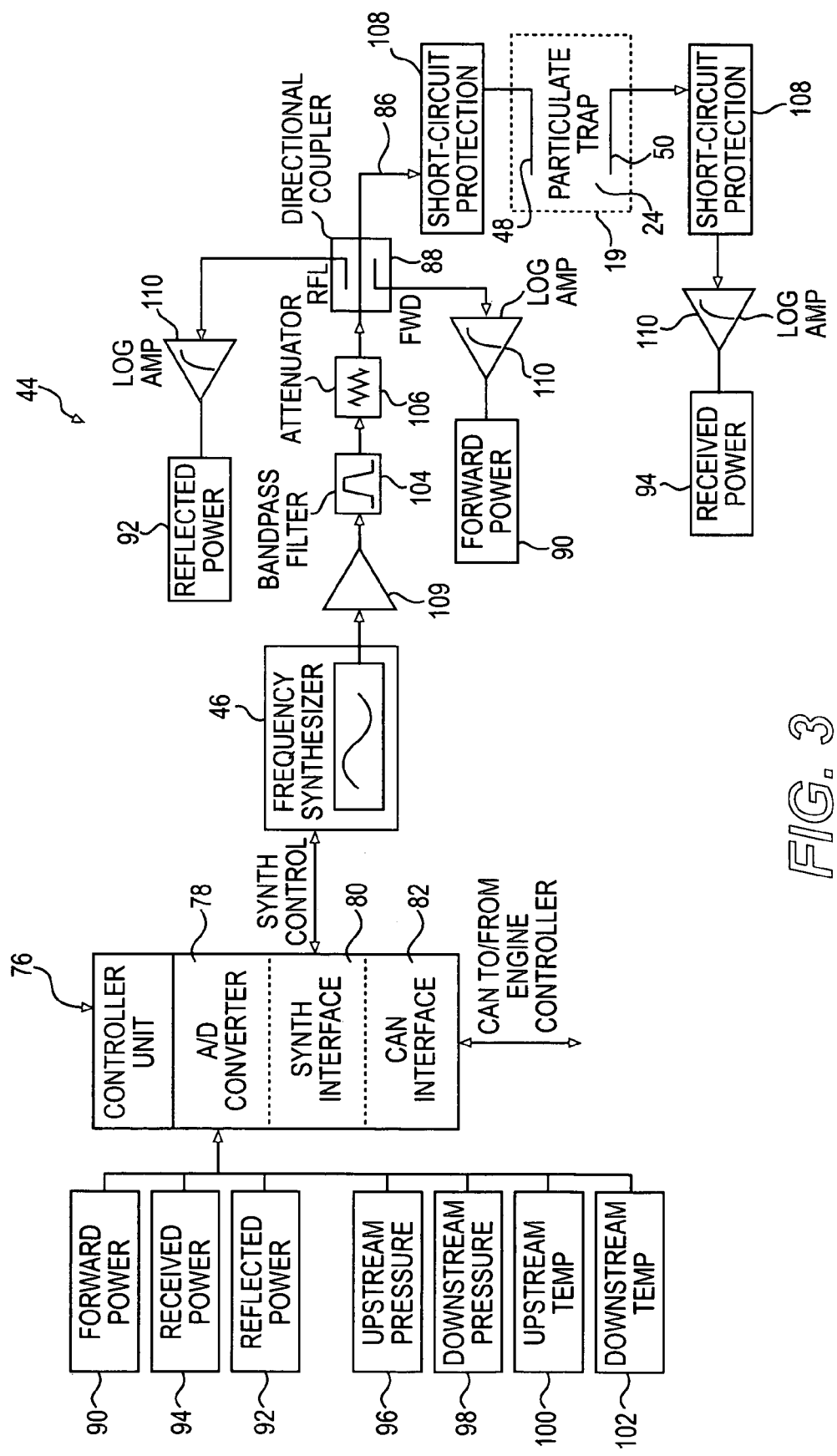
FIG. 3 is a schematic of a particulate loading monitoring system according to an exemplary disclosed embodiment.

FIG. 3 illustrates an exemplary schematic of particulate loading monitoring system 44. Particulate loading monitoring system 44 may include a controller unit 76, which may include multiple components, such as an A/D converter 78 and a synthesizer interface 80. In some embodiments, the functions and components of controller unit 76 may be incorporated into controller 28. In other embodiments, controller unit 76 may be separate from controller 28. In such embodiments, controller unit 76 may include a Controller Area Network (CAN) interface 82 configured to enable communication with one or more other components, such as controller 28, via a CAN datalink or any other suitable datalink or communication format.

Synthesizer interface 80 may be configured to enable communication with and thereby control of frequency synthesizer 46. Synthesizer 46 may be configured to deliver RF signals to particulate trap 19, as discussed above, along an interconnect 86, such as a wire, cable, etc. Particulate loading monitoring system 44 may include a directional coupler 88 configured to monitor RF signals traveling in both directions along interconnect 86. As such, directional coupler 88 may be configured to measure the amount of RF power delivered to transmitting probe 48 ("Forward Power" 90). Particulate loading monitoring system 44 may be further configured to relay this measurement of forward power back to controller unit 76. Directional coupler 88 may also be configured to measure the amount of RF power reflected by transmitting probe 48 ("Reflected Power" 92). Particulate loading monitoring system 44 may be further configured to relay this measurement of reflected power back to controller unit 76. Particulate loading monitoring system 44 may also be configured to measure the amount of RF power received by receiving probe 50 ("Received Power" 94) and relay this measurement back to controller unit 76. From these measurements of forward power and received power, controller unit 76 may determine the amount of power loss (i.e., RF signal loss) across filter medium 24 of particulate trap 19.

Other aspects of system 16 may also be measured, such as upstream pressure (96), downstream pressure (98), upstream temperature (100), and downstream temperature (102). These and/or other measurements may also be forwarded to controller unit 76 to provide further information from which to assess the amount of particulate matter accumulated in particulate trap 19.

Particulate loading monitoring system 44 may include other signal processing components, as shown in an exemplary fashion in FIG. 3. For example, particulate loading monitoring system 44 may include a bandpass filter 104, one or more attenuators 106, one or more short circuit protection devices 108, one or more amplifiers 109, and/or one or more log amps 110.

Figure 4:
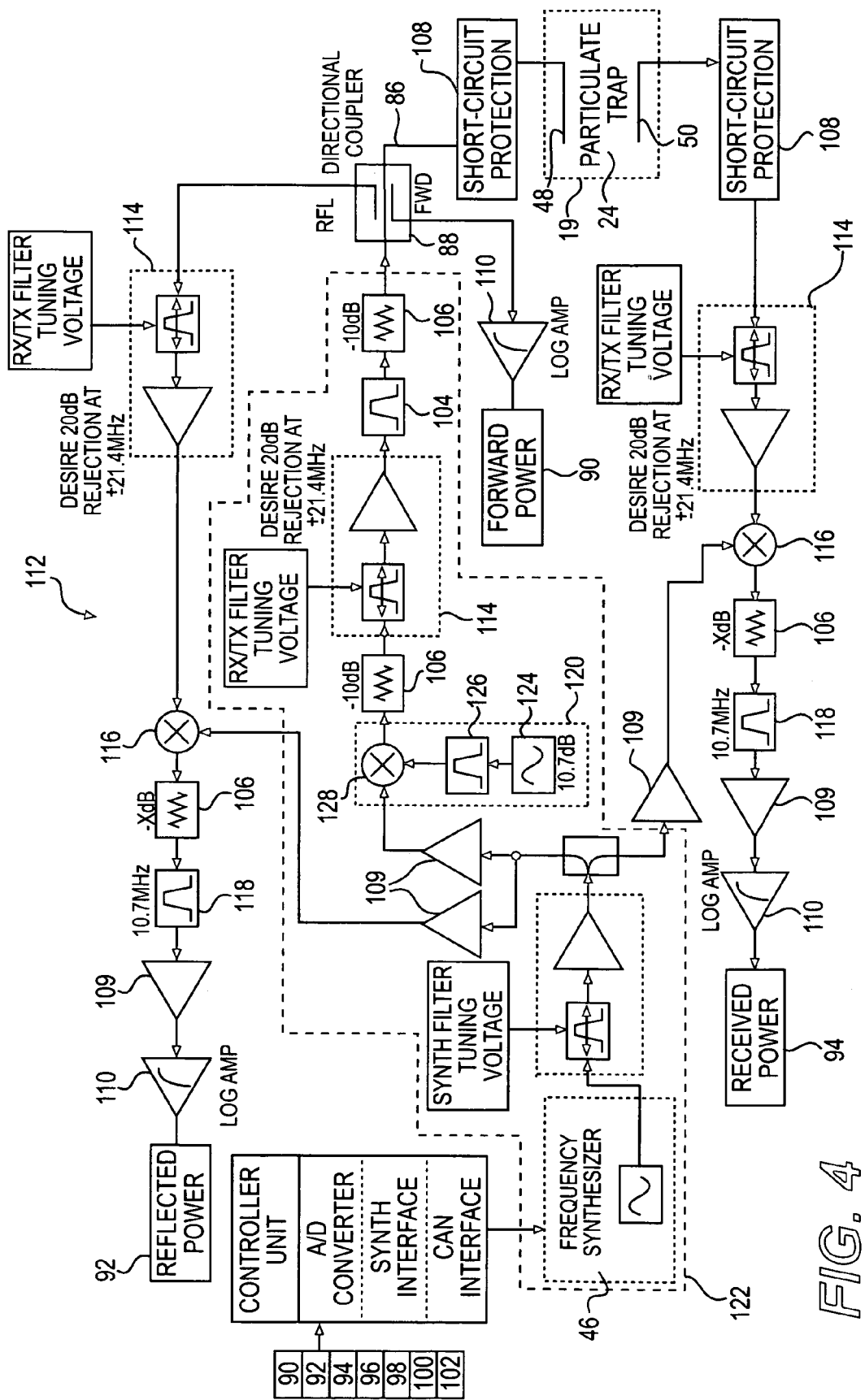
FIG. 4 is a schematic of a narrowband particulate loading monitoring system according to an exemplary disclosed embodiment.

In some embodiments, particulate loading monitoring system 44 may be further configured to filter out all received RF signals except for signals within a predetermined band of frequencies that correspond with the frequencies of the signals transmitted by transmitting probe 48. FIG. 4 illustrates an exemplary schematic of a narrowband particulate loading monitoring system 112. Filtering of the received RF signals may prevent interference from other RF signals from external sources that may be detected by receiving probe 50 but fall outside the predetermined range of frequencies within which particulate loading monitoring system 44 is designed to operate.

Narrowband system 112 may include many or all of the components of particulate loading monitoring system 44 shown in FIG. 3, and may further include additional signal processing and/or filtering components. For example, narrowband system 112 may include one or more tunable bandpass filters 114, one or more frequency mixers 116, one or more narrow bandpass filters 118, and an injection oscillator 120.

Tunable bandpass filters 114 may be employed to filter out at least a portion of received RF signals that are outside of the desired frequency band. Frequency mixers 116 may be employed to convert a frequency swept RF signal to a single frequency, e.g., 10.7 MHz. Such conversion may facilitate further signal processing. Narrow bandpass filters 118 may be employed to filter out signals that are not within a small margin of error from the single frequency, for example, within 100-200 KHz of 10.7 MHz.

Narrowband system 112 may include a tracking signal generator 122. In such narrowband embodiments, synthesizer 46 may produce an offset frequency from that to be transmitted by transmitting probe 48. The offset signal may be directed to frequency mixers 116 for conversion of the received signal and the reflected signal. Injection oscillator 120 may be employed to convert the offset signal to the desired signal before being delivered to transmitting probe 48. To make such a conversion, injection oscillator 120 may include an oscillator 124 (e.g., 10.7 MHz), a bandpass filter 126, and a frequency mixer 128. The offset signal may be mixed with signal from oscillator 124 to produce a tracking signal to be applied to transmitting probe 48. Narrowband system 112 may also include various other signal processing devices, such as bandpass filters 104, attenuators 106, amplifiers 109, log amps 110, etc.

INDUSTRIAL APPLICABILITY

The disclosed particulate trap regeneration system 16 may be suitable to enhance exhaust emissions control for engines. System 16 may be used for any application of an engine. Such applications may include, for example, stationary equipment such as power generation sets, or mobile equipment, such as vehicles. The disclosed system may be used for any kind of vehicle, such as, for example, automobiles, machines (including those for on-road, as well as off-road use), and other heavy equipment.

The presently disclosed system may be mounted on board any type of stationary or mobile equipment. In order for the components of the disclosed system to be sized appropriately for on board incorporation, the system may be configured to generate and measure RF signals only in the specific range of frequencies with which the system is designed to operate, rather than being configured to generate a much wider range of frequencies. By focusing the capabilities of the system components in such a manner, the size of one or more system components may be scaled down. Focused capabilities and smaller size of system components may make particulate loading monitoring by an RF measurement technique practical in terms of cost and size.

An exemplary method of regenerating particulate trap 19 may include determining an amount of particulate matter trapped in filter medium 24 of particulate trap 19. Such a determination may be accomplished by transmitting radio frequency signals of predetermined magnitude and predetermined frequency toward filter medium 24 and receiving and measuring the magnitude of received radio frequency signals that pass through filter medium 24. The method may also include taking a temperature measurement indicative of a temperature of particulate trap 19 at the time the radio signals are received and determining, based on the measured magnitude of received radio frequency signals, a particulate loading value indicative of the amount of particulate matter trapped in filter medium 24.

The method may also involve performing a temperature compensation including modifying, based on the temperature measurement, at least one of the following: the measured magnitude of the received radio frequency signals that pass through filter medium 24 or the particulate loading value. The temperature compensation may involve a function based on the temperature measurement and at least one of the following: the measured magnitude of the received radio frequency signals that pass through the filter medium or the particulate loading value. An example of such a function may be a third order polynomial. Alternatively, the temperature compensation may include referring to a look-up table based on the temperature measurement and at least one of the following: the measured magnitude of the received radio frequency signals that pass through the filter medium or the particulate loading value.

The radio frequency signals that are transmitted toward filter medium 24 may have frequencies of less than about 500 MHz. An exemplary band of frequencies that may be transmitted may be about 100-400 MHz. In choosing the range of radio frequencies to be used herein, a number of considerations may be evaluated. For example, the amount of transmission loss over the selected frequency range should provide for, among other things, suitable measurement sensitivity (i.e., attenuation per unit of particulate matter present) and a more linear response as a function of radio frequency signal attenuation than is possible at a single frequency. The selected range of frequencies should also avoid problems associated with power source frequency drift with time. Further, averaging reduces the effects of temperature on accumulated particulate matter and filter permittivity, which would otherwise require temperature compensation in single or narrow band frequency methods. In addition, lower frequencies mean lower signal attenuation (i.e., less signal loss) and lower device costs.

The method may further include determining a signal loss value by comparing the measured magnitude of the received signals of one or more frequencies to the magnitude of the transmitted signals of the same one or more frequencies. Where a signal loss value is determined, performing the temperature compensation may include modifying the signal loss value based on the temperature measurement.

The method may include delivering radio frequency signals to transmitting probe 48 and detecting magnitudes of radio frequency signals reflected by transmitting probe 48. The method may further include determining the amount of particulate matter trapped in filter medium 24 based on the detected magnitudes of radio frequency signals reflected by transmitting probe 48.

The method may include filtering out all received radio frequency signals except for signals within a predetermined band of frequencies that correspond with the frequencies of the signals transmitted by transmitting probe 48. The method may also include communicating between controller 28 and at least one other component of particulate trap regeneration system 16 via a datalink.

The method may also include activating regeneration device 25 in response to a determination that more than a predetermined amount of particulate matter is trapped in filter medium 24 to thereby reduce an amount of particulate matter in particulate trap 19. The method may further include activating regeneration device 25 in response to one or more other trigger conditions.

In some embodiments, the system may be configured to activate regeneration device 25 when more than one trigger condition is met. For example, the system may wait until both a particulate loading threshold and a time-based trigger condition are met before initiating a regeneration event. In other embodiments, the system may be configured to initiate a regeneration event when the first of multiple possible trigger conditions is met.

The following is a description of an exemplary system that is configured to initiate a regeneration event when the first of multiple possible trigger conditions is met. In such a system, for example, a simple time trigger (e.g., engine operation time) may provide the utmost reliability as no physical characteristics need to be sensed to monitor such a trigger condition. However, depending on other factors, particulate loading in particulate trap 19 may reach a level warranting regeneration at an earlier time than the interval at which the time trigger is set. In order to prevent damage that could result from such a situation, a backpressure or pressure differential trigger may be configured to monitor for relatively higher levels of particulate loading. Thus, in such cases where particulate loading has prematurely reached a high level, a backpressure or pressure differential trigger may trigger regeneration to remedy excessive particulate loading even before a time trigger condition is met.

If, for whatever reason, particulate loading has prematurely reached a high level, but has not caused a significant increase in backpressure, an actual particulate loading monitoring system may detect the actual amount of particulate matter accumulated in filter medium 24. That is, system 16 may, in some embodiments, be configured to measure the amount of particulates accumulated in particulate trap 19 and initiate a regeneration event if the amount of particulates accumulated in particulate trap 19 is above a predetermined threshold level.

If, however, neither the backpressure trigger, nor the particulate loading monitoring system successfully detect excessive particulate loading in a given circumstance, then the time trigger may serve to insure that regeneration occurs at relatively conservative intervals. Further, regeneration may be triggered manually if, for whatever reason, no other trigger conditions are determined to be met, but an operator, owner, service technician, etc. deems that a regeneration may be appropriate based on their own observations.

It will be apparent to those having ordinary skill in the art that various modifications and variations can be made to the disclosed radio frequency-based particulate loading monitoring system without departing from the scope of the invention. Other embodiments of the invention will be apparent to those having ordinary skill in the art from consideration of the specification and practice of the invention disclosed herein. It is intended that the specification and examples be considered as exemplary only, with a true scope of the invention being indicated by the following claims and their equivalents.

What is claimed is:

1. A particulate trap regeneration system, comprising:
a particulate trap having a filter medium configured to remove one or more types of particulate matter from an exhaust flow of an engine;
a regeneration device configured to reduce an amount of particulate matter in the particulate trap; and
a radio frequency-based particulate loading monitoring system configured to determine an amount of particulate matter trapped by the filter medium, the particulate loading monitoring system including:
at least one radio frequency transmitting probe configured to transmit radio frequency signals of predetermined magnitude and predetermined frequency toward the filter medium;
at least one radio frequency receiving probe configured to receive and measure the magnitude of received radio frequency signals that pass through the filter medium;
a temperature sensing device configured to take a temperature measurement indicative of a temperature of the particulate trap at the time the radio signals are received by the receiving probe; and
a controller configured to:
determine, based on the measured magnitude of received radio frequency signals, a particulate loading value indicative of the amount of particulate matter trapped in the filter medium;
perform a temperature compensation including modifying, based on the temperature measurement, at least one of the following:
the measured magnitude of the received radio frequency signals that pass through the filter medium; or
the particulate loading value; and
activate the regeneration device in response to the particulate loading monitoring system detecting more than a predetermined amount of particulate matter trapped in the filter medium.

2. The system of claim 1, wherein the controller is configured to modify the measured magnitude of the received radio frequency signals that pass through the filter medium.

3. The system of claim 1, wherein the controller is further configured to determine a signal loss value by comparing the measured magnitude of the received signals of one or more frequencies to the magnitude of the transmitted signals of the same one or more frequencies, and wherein performing the temperature compensation includes modifying the signal loss value based on the temperature measurement.

4. The system of claim 1, wherein the temperature compensation involves a function based on the temperature measurement and at least one of the following:
the measured magnitude of the received radio frequency signals that pass through the filter medium; or
the particulate loading value.

5. The system of claim 4, wherein the function is a third order polynomial.

6. The system of claim 1, wherein the temperature compensation involves a look-up table based on the temperature measurement and at least one of the following:
the measured magnitude of the received radio frequency signals that pass through the filter medium; or
the particulate loading value.

7. The system of claim 1, wherein the radio frequency signals have a frequency of less than about 500 MHz.

8. The system of claim 1, further including:
a radio frequency synthesizer configured to deliver radio frequency signals to the radio frequency transmitting probe;
wherein the particulate loading monitoring system is further configured to detect magnitudes of radio frequency signals reflected by the radio frequency transmitting probe and determine the amount of particulate matter trapped in the filter medium based on the detected magnitudes of radio frequency signals reflected by the radio frequency transmitting probe.

9. The system of claim 1; wherein the system is further configured to filter out all received radio frequency signals except for signals within a predetermined band of frequencies that correspond with the frequencies of the signals transmitted by the radio frequency transmitting probe.

10. The system of claim 1, wherein the controller is further configured to communicate with at least one other component of the particulate trap regeneration system via a datalink.

11. A method of regenerating a particulate trap, comprising:
determining an amount of particulate matter trapped by a filter medium of a particulate trap configured to remove one or more types of particulate matter from an exhaust flow of an engine by:
transmitting radio frequency signals of predetermined magnitude and predetermined frequency toward a filter medium;
receiving and measuring the magnitude of received radio frequency signals that pass through the filter medium;
taking a temperature measurement indicative of a temperature of the particulate trap at the time the radio signals are received;
determining, based on the measured magnitude of received radio frequency signals, a particulate loading value indicative of the amount of particulate matter trapped in the filter medium;
performing a temperature compensation including modifying, based on the temperature measurement, at least one of the following:
the measured magnitude of the received radio frequency signals that pass through the filter medium; or
the particulate loading value; and
activating a regeneration device, configured to reduce an amount of particulate matter in the particulate trap, in response to the particulate loading monitoring system detecting more than a predetermined amount of particulate matter trapped in the filter medium.

12. The method of claim 11, wherein the method includes modifying the measured magnitude of the received radio frequency signals that pass through the filter medium.

13. The method of claim 11, further including determining a signal loss value by comparing the measured magnitude of the received signals of one or more frequencies to the magnitude of the transmitted signals of the same one or more frequencies, and wherein performing the temperature compensation includes modifying the signal loss value based on the temperature measurement.

14. The method of claim 11, wherein the temperature compensation involves a function based on the temperature measurement and at least one of the following:
the measured magnitude of the received radio frequency signals that pass through the filter medium; or
the particulate loading value.

15. The method of claim 14, wherein the function is a third order polynomial.

16. The method of claim 11, wherein the temperature compensation involves a look-up table based on the temperature measurement and at least one of the following:
the measured magnitude of the received radio frequency signals that pass through the filter medium; or
the particulate loading value.

17. The method of claim 11, wherein the radio frequency signals have a frequency of less than about 500 MHz.

18. The method of claim 11, further including:
delivering radio frequency signals to a radio frequency transmitting probe;
detecting magnitudes of radio frequency signals reflected by the radio frequency transmitting probe; and
determining the amount of particulate matter trapped in the filter medium based on the detected magnitudes of radio frequency signals reflected by the radio frequency transmitting probe.

19. The method of claim 11, further including filtering out all received radio frequency signals except for signals within a predetermined band of frequencies that correspond with the frequencies of the signals transmitted by the radio frequency transmitting probe.

20. The method of claim 11, further including communicating with at least one other component of the particulate trap regeneration system via a datalink.

21. A machine comprising:
a frame;
an exhaust flow producing engine mounted to the frame; and
a particulate trap regeneration system, including:
a particulate trap having a filter medium configured to remove one or more types of particulate matter from an exhaust flow of an engine;
a regeneration device configured to reduce an amount of particulate matter in the particulate trap; and
a radio frequency-based particulate loading monitoring system configured to determine an amount of particulate matter trapped by the filter medium, the particulate loading monitoring system including:
at least one radio frequency transmitting probe configured to transmit radio frequency signals of predetermined magnitude and predetermined frequency toward the filter medium;
at least one radio frequency receiving probe configured to receive and measure the magnitude of received radio frequency signals that pass through the filter medium;
a temperature sensing device configured to take a temperature measurement indicative of a temperature of the particulate trap at the time the radio signals are received by the receiving probe; and
a controller configured to:
determine, based on the measured magnitude of received radio frequency signals, a particulate loading value indicative of the amount of particulate matter trapped in the filter medium;
perform a temperature compensation including modifying, based on the temperature measurement, at least one of the following:
the measured magnitude of the received radio frequency signals that pass through the filter medium; or
the particulate loading value; and
activate the regeneration device in response to the particulate loading monitoring system detecting more than a predetermined amount of particulate matter trapped in the filter medium.

22. The machine of claim 21, wherein the controller is further configured to determine a signal loss value by comparing the measured magnitude of the received signals of one or more frequencies to the magnitude of the transmitted signals of the same one or more frequencies, and wherein performing the temperature compensation includes modifying the signal loss value based on the temperature measurement.

23. The machine of claim 21, wherein the temperature compensation involves a third order polynomial function based on the temperature measurement and at least one of the following:
the measured magnitude of the received radio frequency signals that pass through the filter medium; or
the particulate loading value.

24. The machine of claim 21, wherein the temperature compensation involves a look-up table based on the temperature measurement and at least one of the following:
the measured magnitude of the received radio frequency signals that pass through the filter medium; or
the particulate loading value.

25. The machine of claim 21, further including:
a radio frequency synthesizer configured to deliver radio frequency signals to the radio frequency transmitting probe;
wherein the particulate loading monitoring system is further configured to detect magnitudes of radio frequency signals reflected by the radio frequency transmitting probe and determine the amount of particulate matter trapped in the filter medium based on the detected magnitudes of radio frequency signals reflected by the radio frequency transmitting probe.

26. The machine of claim 21, wherein the system is further configured to filter out all received radio frequency signals except for signals within a predetermined band of frequencies that correspond with the frequencies of the signals transmitted by the radio frequency transmitting probe.

27. The machine of claim 21, wherein the controller is further configured to communicate with at least one other component of the particulate trap regeneration system via a datalink.

* * * * *